United States Patent [19]

Swetly et al.

[11] Patent Number: 4,820,638
[45] Date of Patent: Apr. 11, 1989

[54] NOVEL ALPHA INTERFERON SPECIES PRODUCED BY RECOMBINANT MEANS

[75] Inventors: Peter Swetly; Eva Dworkin-Rastl; Peter Meindl, all of Vienna, Austria

[73] Assignee: Dr. Karl Thomae GmbH, Fed. Rep. of Germany

[21] Appl. No.: 495,944

[22] Filed: May 19, 1983

[30] Foreign Application Priority Data

May 28, 1982 [DE] Fed. Rep. of Germany ....... 3220116

[51] Int. Cl.$^4$ ...................... C12N 1/20; C12N 15/00; C12P 21/00; C12P 21/02
[52] U.S. Cl. ...................... 435/68; 435/70; 435/172.3; 435/252.33; 435/320; 530/350; 424/85.7; 536/27
[58] Field of Search ..................... 435/172.2, 172.3, 68, 435/253, 317, 70, 320; 536/27, 28, 29; 514/12; 530/350; 424/85

[56] References Cited

U.S. PATENT DOCUMENTS

4,433,140  2/1984  Seliger et al. ..................... 536/27
4,530,901  7/1985  Weissman ......................... 435/70

OTHER PUBLICATIONS

Taniguchi et al., *Proc. Natl. Acad. Sci.*, vol. 77(9), pp. 5230–5233, Sep. 1980, "Expression of the Human Fibroblast Interferon Gene in *Escherichia coli*".

Taniguchi et al., *Nature*, vol. 285, pp. 547–549, Jun. 19, 1980, "Human Leukocyte and Fibroblast Interferons are Structurally Related".

Taniguchi et al., *Proc. Natl. Acad. Sci.*, vol. 77(7), Jul. 1980, pp. 4003–4006, "Molecular Cloning of Human Interferon cDNA".

Ohno et al., *Proc. Natl. Acad. Sci.*, vol. 78(9) Sep. 1981, pp. 5305–5309, "Structure of a Chromosomal Gene for Human Interferon β".

Dcrynck et al., *Nature*, vol. 285, Jun. 1980, pp. 542–546, "Isulation and Structure of a Chromosomal Gene for Human Interferon β".

Bodo, Gerhard, *Methods in Enzymology*, vol. 78 (A) Edited by Sidney Pestka, 1981, pp. 69–75.

Dworkin-Rastl et al, *Journal of Interferon Research*, vol. 2, No. 4, 1982, "Molecular Cloning of Human Alpha and Beta Interferon Genes from Namalwa Cells", pp. 575–585.

Adolf et al. *Journal of Interferon Research*, vol. 2, No. 2, 1982, "Interferon Production in Human Hematopoietic Cell Lines: Response to Chemicals and Characterization of Interferons", pp. 261–270.

Goeddel et al., *Nature*, vol. 287, 1980, "Human Leukocyte Interferon Produced by *E. coli* is Biologically Active," pp. 411–416.

S. Eckhardt, et al., *Oncology*, Jun. 1985, pp. 1–2.

R. Kuzmits et al., *Oncology*, 42: Suppl. 1, pp. 26–32 (1985).

J. Th. P. Janssen et al., *Oncology*, 42: Suppl. 1, pp. 3–6 (1985).

H. P. Zenner, et al., *Oncology*, 42: suppl. 1, pp. 15–18 (1985).

J. B. Lippincott Co., *Cancer*, vol. 58, No. 12, Dec. 15, 1986.

Shibasaki, et al., *J. Clin. Invest.*, 76:378–380 (1985).

Chen, et al., *Virology*, 155:106–119 (1986).

Jornvall, et al., *Proc. Natl. Acad. Sci, USA*, 81:3024–3028 (1984).

Grutter, et al., *Naturwissenschaften*, 70:434–438 (1983).

Stanway, et al., *Proc. Natl. Acad. Sci., USA*, 81:1539–1543 (1984).

Manos, et al., *Molecular and Cellular Biology*, pp. 1125–1133 (1984).

R. Camble, et al., *Biochemical and Biophysical Research Communications*, 134:1404–1411 (1986).

*Primary Examiner*—Thomas G. Wiseman
*Assistant Examiner*—Robin Teskin
*Attorney, Agent, or Firm*—Saidman, Sterne, Kessler & Goldstein

[57] ABSTRACT

A novel species of alpha interferon is taught. The alpha interferon amino acid sequence is disclosed and a gene corresponding thereto. The alpha interferon gene is expressed in *Escherichia coli*.

8 Claims, 6 Drawing Sheets

FIG. 1 mRNA 5'————— CAGTTCCAGAAGG —————3'~~poly(A)

cDNA 3'————— GTCAAGGTCTTCC-$^{32}$P5'

NOVEL ALPHA INTERFERON SPECIES PRODUCED BY RECOMBINANT MEANS

BACKGROUND OF THE INVENTION

1. Field of the Invention

This invention relates to a process for the simultaneous identification of Interferon-α and Interferon-β gene expression vehicles, and the probe employed in that identification process.

2. Description of the Prior Art

Three types of human interferon are known from the literature, namely leucocyte interferon (interferon-α, abbreviated to IFN-α), fibroblast interferon interferon-β, abbreviated to IFN-β) and immune interferon (interferon-γ, abbreviated to IFN-γ) (see W. E. Stewart II, "The Interferon System," Springer-Verlag Vienna/-New York, 2nd edition (1981)). Human leucocytes or human myelobastoid cells stimulated with a virus produce leucocyte interferon, human fibroblasts which are induced with a virus or a suitable nucleic acid produce fibroblast interferon and human T-lymphocytes which are induced with mitogen, e.g. concanavalin, produce immune interferon.

It is also known that human cells of the B-lymphocyte type, as represented, for example, by the cell strains NC-37, Namalwa, Akuba or RPMI 1788, produce leucocyte interferon and fibroblast interferon simultaneously when stimulated by a virus (see Journal of General Virology 38, 51–59 (1977)). The proportions of IFN-α and IFN-β produced can be varied by the choice of induction conditions (see Journal of Interferon Research 2, in preparation (1982)). For example, the following proportions of IFN-α and IFN-β are obtained from different cell strains induced with Sendai virus:

| Cell strain | Percentage of interferon activity neutralized by specific antisera against | | |
|---|---|---|---|
| | IFN-α | IFN-β | IFN-α + IFN-β |
| Namalwa | 52 | 34 | ≧98 |
| NC-37 | 40 | 52 | ≧97 |
| Akuba | 85 | 27 | ≧98 |
| RPMI 1788 | 68 | 29 | ≧98 |

Moreover, molecular cloning of IFN-α genes from leucocytes (see Nature 284, 316–320 (1980); Science 209, 1343–1347 (1980) and EP-A1 No. 0.032.134) and from myelobastoid cells (see Nature 287 411–416 (1980), ibid 290, 20–26 (1981) and GB-A No. 2.079.291) gave the result that IFN-α is coded by a family of genes which consists of at least 10 distinguishable genes and this in turn means that the gene products of these DNA sequences do not constitute a single uniform protein; this means that IFN-α is a mixture of similar proteins. These sub-types are referred to in the literature as IFN-α 1,2,3 . . . (see Nature 287, 401–408 (1980) and Gene 15, 379–394 (1981)) or LeIFN A,B,C . . . (see Nature 290, 20–26 (1981)).

On the other hand, a uniform DNA sequence was found for IFN-β; this means that only a single gene codes for fibroblast interferon (see Nature 285, 542–547 (1980)).

Although no cross-hybridization takes place between IFN-α genes and the IFN-β gene, contrary to what happens within the IFN-α gene family, the sequences have about 45% homology (see Nature 285, 547–549 (1980)). The longest fragment of sequence is 13 nucleotides long. This tridecanucleotide is known from the literature (see Eur. J. Cell. Biol. 25, 8–9 (1981)). The IFN-α genes containing this tridecanucleotide are LeIFN B,C,D,F,G; only 12 of the 13 nucleotides are present in LeIFN A and H (See Nature 290, 20–26 (1981)).

SUMMARY OF THE INVENTION

Accordingly, it is an object of this invention to provide a process for the simultaneous identification and isolation of IFN-α and IFN-β genes, and expression vehicles containing those genes.

This object can be achieved by employing a radioactively labeled polynucleotide as the probe which is capable of hybridizing with both the IFN-β gene and at least two of the genes for IFN-α.

Expression vehicles containing recombinant DNA synthesized from a matrix of interferon RNA can be conventionally secured by isolation of IFN-mRNA from interferon-producing cells induced with a suitable agent, such as a virus. This matrix is used for the preparation of single stranded cDNA by conventional enzyme synthesis, and a second, complementary DNA strand is thereafter synthesized. The ends of the synthesized DNA are modified for incorporation in the DNA of a host organism, such as a bacteria. The bacteria is allowed to reproduce and express the hybrid plasmid thus obtained.

The offspring containing sequences specific for IFN-α or IFN-β can be subsequently identified by colony hybridization. In this hybridization identification, the probe employed is a polynucleotide capable of hybridization which is common to both gene sets. As only colonies with DNA sequences complementary to the identified polynucleotide will incorporate the labeled probe, these can be identified by autoradiography, thus providing a process where both α- and β-interferon expression vehicle colonies can be easily, simultaneously identified.

BRIEF DESCRIPTION OF THE DRAWINGS

FIG. 6 is a schematic comparison of the restriction maps of four DNA inserts of recombinant DNA molecules according to the invention.

DETAILED DESCRIPTION OF THE INVENTION AND EMBODIMENTS

The process of this invention requires selection of a suitable cell strain which, after induction, e.g. with Sendai virus, produces both IFN-α and also IFN-β. Suitable human cells of the B-lymphocyte type include, for example, the cell strains Namalwa, NC-37, Akuba or RPMI 1788, but preferably the strain Namalwa.

Figure 1:
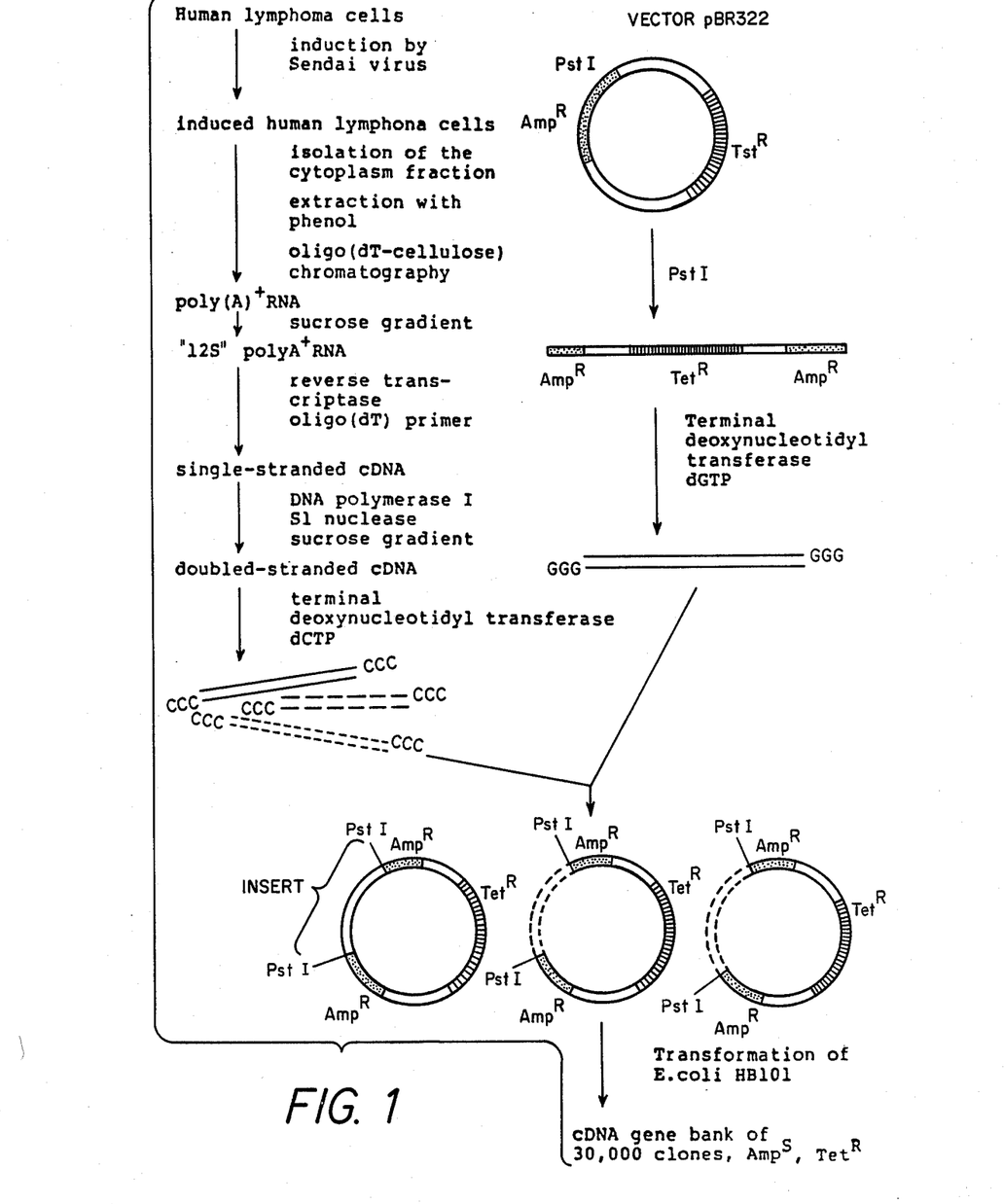
FIG. 1 is a schematic representation of the production of a cDNA clone bank.

The selected cells are appropriately denatured at the moment of maximum IFN-mRNA synthesis, typically 6 to 12 hours, preferably 9 hours, after the virus induction. After the nuclei have been removed, the RNA from the cell cytoplasm is purified by phenol extraction and precipitation with alcohol, and then the poly(A)+-RNA is isolated by oligo (dT) cellulose chromatography and then concentrated by gradient centrifuging with respect to interferon-specific sequences (see left hand column of FIG. 1).

The poly(A)+RNA purified in this way is used as a matrix for the preparation of single-strand cDNA by means of the enzyme reverse transcriptase. The second strand of DNA complementary to this single strand of DNA is synthesized by means of DNA-polymerase I. The cDNA-synthesis and the synthesis of the complementary DNA was carried out in a solution containing a mixture of deoxynucleoside triphosphate of adenosine, thymidine, guanosine and cytidine. The double-stranded cDNA mixture obtained is then modified at both ends of the strands by means of the enzyme Sl nuclease so that any overhanging regions of an individual strand are removed and those double-strand DNA molecules which contain at least 600 base pairs are isolated by gradient centrifuging. The cDNA mixture thus obtained is extended by about 15 nucleotides, by means of the enzyme terminal transferase, by the addition of oligodeoxycytidine at the 3' end of each strand, thus producing one component for the synthesis of recombinant molecules (see the left hand column of FIG. 1).

For the second component, a circular double-strand plasmid, preferably obtained from *Escherichia coli*, e.g., *Escherichia coli* plasmid pBR322, is linearized by means of restriction endonuclease Pst I and is modified, analogously to the cDNA mixture, by the addition of oligodeoxyguanidine to the 3' ends of the molecule so that overhanging ends of oligodeoxyguanidine are formed. These ends can form stable double-strand DNA regions with the free oligodeoxycytidine ends of the cDNA molecules (see the right hand column in FIG. 1).

With the hybrid plasmids thus obtained, e.g. from pBR322 and cDNA, a microorganism is transformed into a host, e.g. *Escherichia coli* HB 101, in which the replication and expression of this DNA occurs.

Among the clones thus produced, those which contain sequences specific to IFN-α or IFN-β are identified by colony hybridization. The test substance used is radioactively labeled cDNA which is synthesized by reverse transcription of RNA containing IFN-mRNA, with the tridecanucleotide 5'dCCTTCTGGAACTG3', which is specific to interferon sequences, as the primer. For this purpose, the tridecanucleotide is radioactively labeled at its end, preferably with γ-$^{32}$P-ATP and T4-polynucleotide kinase. The initiation complex for the reverse transcriptase reaction with an excess of the labelled tridecanucleotide and poly(A)+RNA from cells induced with Sendai virus is prepared under the conditions described hereinbefore (see FIG. 2). A cDNA thus prepared is therefore only radioactively labeled when the initiation complex for the reverse transcriptase reaction with the tridecanucleotide has been produced, since the labeling is contained exclusively in this segment. As a result, the invention ensures high selectivity for the recognition of DNA with a DNA sequence complementary to the tridecanucleotide and thus for the recognition of α- and β-interferon DNA. Those transformed colonies of bacteria which contain hybrid plasmids with DNA sequences complementary to the tridecanucleotide used are shown up by autoradiography (see FIG. 3). In this way, out of about 13,000 transformed bacterial clones, 190 clones which gave a positive signal with the cDNA initiated by the tridecanucleotide with isolated, i.e. about 1% of all the clones in the gene bank contain the specific sequence dCCTTCTGGAACTG.

The interferon-specific nucleic acid sequences in the recombinant DNA molecules are identified by RNA transfer hybridization, hybrid isolation, restriction mapping and nucleic acid sequencing. Biological identification of the interferon polypeptides formed is effected by determining the antiviral activity, whilst the type of interferon is determined by immunological methods.

The interferon genes isolated in this way can then be expressed not only in bacteria, but also in other organisms such as yeast, for example, whilst the insertion of a promoter in conjunction with a ribosome binding sequence makes it possible to obtain values up to about $10^4$ times that of the spontaneous expression.

Thus, with the invention, it has been possible for the first time to achieve the goal according to the invention of isolating two related classes of gene, namely the two classes IFN-α and IFN-β, in a single operation, and demonstrate their suitability for use in the production of interferons, by selecting cells of the B-lymphocyte type as starting material for isolation of the RNA required and using an interferon-specific oligonucleotide as primer for the cDNA used as the hybridization sample.

This invention may be further understood by reference to the following, step-by-step, Examples.

EXAMPLE A

Selection of a suitable cell strain for the production of poly(A)+RNA which contains human IFN-α and IFN-β-mRNA Various human cell strains were induced, with Sendai virus, to produce interferon according to methods known from the literature and after 24 to 48 hours the content of IFN-α and IFN-β was determined from the cell supernatants by neutralization with antisera specific to certain types. The proportions of IFN-α to IFN-β found in some of the cell strains tested are shown in the Table on page 2. It is clear that Namalwa cells produce, for example, rather more than 50% of IFN-α and up to about 50% IFN-β after induction with Sendai virus.

The neutralization test was carried out as follows:

Approximately 10 interferon units from the supernatants of the cell cultures induced with Sendai virus were incubated at 37° C. for 60 to 90 minutes with:

1. Antiserum against IFN-α; final dilution 1:100; (obtained from Research Resources Branch, National Institutes of Allergy and Infectious Diseases, Bethesda, Md, USA).

2. Antiserum against human β-IFN; final dilution 1:300; (obtained from Dr. Y. H. Tan, University of Calgary, Canada).

3. Mixture of 1 and 2.

After incubation, the residual interferon activity was determined in the plaque reduction test (see Journal of Interferon Research 2, in preparation (1982)).

EXAMPLE B

Preparation of poly(A)+RNA containing human IFN-α and IFN-β-mRNA, from Namalwa cells induced with Sendai virus The culture of the Namalwa cells and the induction with Sendai virus were effected according to methods known from the literature (see Methods in Enzymology, Vol. 78A, pages 69-75 (1981), Academic Press, N.Y.). The moment of preparation of the mRNA was chosen to be 9 hours (6 to 12 hours) after the induction with Sendai virus, since after this period the proportion of interferon-specific mRNA reaches a maximum.

The cells were centrifuged for 20 minutes at 1000 g, washed once in NP-40 buffer (0.14 M NaCl, 1.5 mM MgCl$_2$, 10 mM tris-HCl, pH 7.4) and suspended in NP-40 buffer with 0.5% of the non-ionic detergent NP-40 (made by Shell) and 2 mg/ml of bentonite. After 5 minutes in an ice bath, the cell nuclei were pelleted by centrifuging as described above, the cytoplasm (RNA-containing) fraction (supernatant) was extracted three times with phenol-chloroform and once with chloroform, after the addition of 2% SDS, 5 mM of EDTA and 50 mM tris-HCl, and then the RNA was precipitated with alcohol. The poly(A)+RNA was purified using a method known from the literature (Proc. Natl. Acad. Sci. USA, 69, 1408-1412 (1972)) by means of oligo (dT) cellulose chromatography and then divided up according to the size of the molecules by centrifuging in a 5-20% sucrose gradient in 10 mM sodium acetate buffer, pH 5.5, 1 mM EDTA (20 hours at 25,000 rpm with a Spinco SW 27 rotor) and molecules ranging from 6S (sedimentation units) and 18S in size were collected (referred to as "12S-RNA" for the sake of simplicity) (see the left hand side of FIG. 1).

The content of interferon-specific mRNA (IFN-α and IFN-β-mRNA) was determined by microinjection of "12S-RNA" into Xenopus laevis oocytes (see J. Embryol. and Exper. Morph. 20, 401-525 (1968) and by measuring the interferon activity in the oocyte supernatant. 1 μg of injected "12S-RNA" gave an average interferon titre of about 1000 International interferon Units (I.U.) based on the interferon standard 69/19:

| Quantity of "12S"-poly(A) + RNA from Namalwa cells induced with Sendai virus | Units of interferon per ml of oocyte supernatant | Percentage of interferon activity neutralized by antisera against: | |
|---|---|---|---|
| | | IFN-α | IFN-α + IFN-β |
| 1 μg | 1,000 | 80 | >98 |

About 80% of this activity could thus be neutralized by antiserum against α-type interferon, whereas the entire activity could only be neutralized by a mixture of anti-α and anti-β-interferon antiserum.

EXAMPLE C

Preparation of a Namalwa-cDNA clone bank

Poly(A)+RNA with a molecular size of between 6 and 18S ("12S-RNA") (see Example B) was used as a matrix for the preparation of single-strand cDNA, by incubating 40 μg/ml of poly(A)+RNA in 50 mM of tris-HCl, pH 8.3, 10 mM of MgCl$_{12}$, 100 mM of KCl, 1 mM of dNTPS, 0.4 mM of DTT, 4 mM of Na pyrophosphate, 20 μg/ml of oligo(dT)$_{12-18}$ (PL-Biochemicals), 25 μg/ml of actinomycin D with 100 units/ml of AMV reverse transcriptase (Dr. J. Beard, Life Sciences, Inc. 1509½ 49th Street, South, St. Petersburg, Fla. 33707, USA) at 44°-45° C. for 45 minutes. Then the RNA part of the RNA-DNA hybrid was removed by incubation for 1 hour in 0.3 M of NaOH at 50° C., after which the single-stranded cDNA was neutralized and precipitated with ethanol.

The second DNA strand complementary to the single strand of DNA was synthesized under the following conditions: 30 μg/ml of single stranded cDNA was incubated for 6 hours at 15° C. in 0.12 M of potassium phosphate buffer, pH 6.9, 10 mM of MgCl$_2$, 10 mM of DTT, 1 mM of dNTPs with 300 units/ml of DNA polymerase I (Boehringer Mannheim), then extracted with phenol and precipitated with ethanol.

The double-stranded cDNA mixture thus prepared was modified at both ends of the strands so that any overhanging single strand regions were removed. For this, the DNA was incubated for 30 minutes at 37° C. in 0.3 M of NaCl, 30 mM of sodium acetate, pH 4.5, 1 mM of ZnCl$_2$ with 1250 units per ml of Sl-nuclease (Miles Laboratories), then extracted with phenol and precipitated with ethanol. The "blunt ended" double-stranded cDNA thus produced was separated on a 5-20% sucrose gradient in 10 mM of sodium acetate buffer, pH 5.5, and 1 mM of EDTA, and those fractions having a length of at least 600 base pairs were isolated.

Of this cDNA mixture, 0.5 μg were extended by about 15 nucleotides by the addition of oligodeoxycytidine at the 3' end of each strand, by incubation in 140 mM of potassium cacodylate, pH 6.9, 30 mM of tris-HCl, pH 6.9, 2 mM of CoCl$_2$, 0.1 mM of DTT, 0.1 mg/ml of BSA and 5 μm of dCTP with 500 units/ml of terminal transferase at 37° C. for 4 minutes. In this step, the cDNA mixture which forms one component of the recombinant molecules is prepared (see the left hand side of FIG. 1).

The second component was Escherichia coli plasmid pBR322, a circular double-stranded DNA molecule. One aliquot of 2 μg pBR322 was linearized by means of the restriction endonuclease Pst I and was modified, in a similar manner to the cDNA mixture, by the addition of oligodeoxyguanidine to the 3'ends of the molecule so as to produce protruding oligodeoxyguanidine termini (the right hand side of FIG. 1). These oliogodeoxyguanidine termini are capable of producing stagble DNA double-strand regions by base pairing with the free oligodeoxycytidine termini of the cDNA molecules. For this, the two components of this reaction are incubated in 0.1 M of NaCl, 1 mM of EDTA, 20 mM of tris-HCl, pH 8, at 65° C. for 10 minutes then at 45° C. for 2.5 hours and then at 37° C. overnight.

Using this method, the Pst I restriction endonuclease break is regenerated and can subsequently be used to cut the cDNA inserts out of the vector hybrid.

The hybrid plasmids produced by this method from pBR322 and Namalwa-cDNA were used to transform Escherichia coli HB 101 by the method known from the literature (Proc. Natl. Acad. Sci., USA 69, 2110-2114 (1972)). In this way, 30,000 clones of transformed Escherichia coli cells were obtained and were divided up individually in microtitre plates.

EXAMPLE D

Preparation of a hybridization sample which is specific in terms of IFN-α and IFN-β DNA sequences, using a synthetic tridecanucleotide 5'dCCTTCTGGAACTG3'

The method of selection for transformed Escherichia coli clones containing interferon sequences, to which this invention relates, is based on the use of a synthetic tridecanucleotide with the sequence: 5'dCCTTCTGGAACTG3'. This sequence constitutes the longest uninterrupted DNA segment in which there is homology between the majority of the IFN-α genes and IFN-β gene. The synthesis of the tridecanucleotide can be achieved through conventional methods. A method of synthesis is also disclosed in pending U.S. patent application No. 351,851, filed Feb. 24, 1982. That portion of the referenced application is incorporated herein by reference. The tridecanucleotide was kept in 50 mM of tris-HCl, pH 7.5, 10 mM of MgCl$_2$, 5 mM of DTT, 0.1 mM of spermidine, 1 μm of 32P-ATP with 60 units/ml of T4-polynucleotide kinase (Bethesda Research Laboratories) at 37° C. for 30 minutes in order to label it with a specific activity of 500 Ci/mMol at the 5' end of the molecule.

Figure 2:
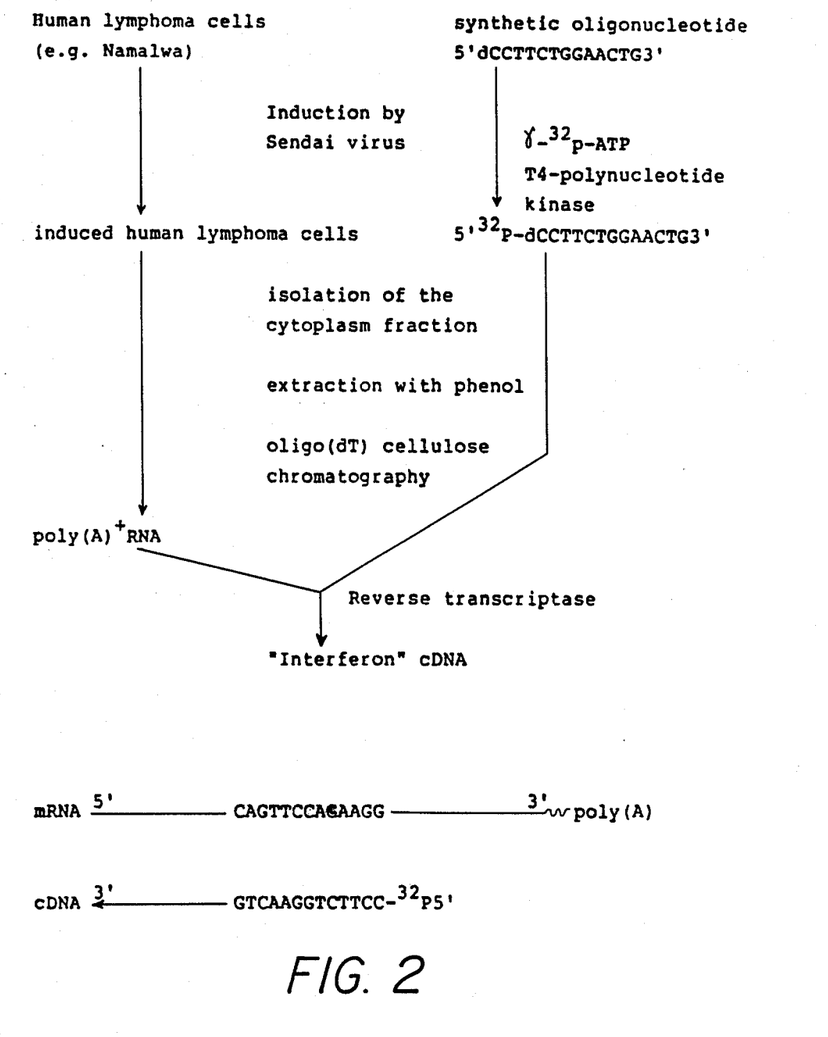
FIG. 2 is a schematic representation of the preparation of a hybridization probe incorporating a labeled polynucleotide common to IFN-α and IFN-β genes.

This terminally labeled tridecanucleotide was used as a primer for (single-stranded) cDNA synthesis, whilst poly(A)+RNA from Namalwa cells induced with Sendai virus (see Example B) was used as the matrix. The reaction was carried out with a 5-10-fold molar excess of primer relative to the RNA in 50 mM of tris-HCl, pH 8.3, 60 mM of KCl, 5 mM of DTT, 50 μg/ml of actinomycin D, 4 mM of MgCl$_2$, 4 mM of sodium pyrophosphate and 0.5 mM of dNTPs with 100 units/ml of AMV reverse transcriptase for 90 minutes at 37° C. After the RNA component of the RNA-DNA hybrid has been removed by incubation for 1 hour in 0.3 M of NaOH at 50° C. and subsequent neutralization with 0.3 M acetic acid, the cDNA can be used as a hybridization sample. A schematic representation of this process is shown in FIG. 2. A cDNA prepared in this way thus carries the radio-labeling only in molcules which have been synthesized from interferon-specific tridecanucleotide as the primer and thus shows high specificity for the recognition of interferon-DNA sequences in hybridizations.

EXAMPLE E

Colony hybridization with tridecanucleotide-primed cDNA

Figure 3:
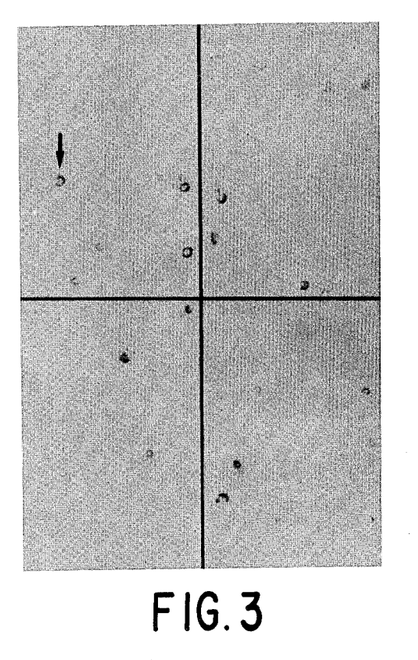
FIG. 3 is an autoradiograph of a colony hybridization of a clone bank employing a labeled polynucleotide as the probe.

The method described here is used for the recognition of those transformed bacteria clones which contain hybride plasmids with DNA sequences complementary to the tridecanucleotide. For this, cells of individually cloned transformants were transferred onto 22×15 cm nitrocellulose filter (pore size 0.45 μm, Millipore or Schleicher & Schuell), bred on the filters to form a colony 2 mm in diameter and then prepared for colony hybridization according to the method known from the literature (Proc. Natl. Acad. Sci., USA 72, 3961-3965 (1975) and Analytical Biochemistry 98, 60-63 (1979)). Nucleic acid hybridization with terminally labeled cDNA (see Example D) was carried out in 50% formamide, 4×SET (1×SET=0.15 M NaCl, 5 mM EDTA, 50 mM of tris-HCl, pH 8), 1×Denhardt's solution (0.02% BSA, 0.02% ficoll, 0.02% polyvinylpyrrolidone), 0.5 mg/ml of denatured and sheared salmon sperm DNA, 0.1% sodium pyrophosphate and 0.1% SDS for 48 hours at 37° C. The filters were then washed for several hours (6 to 8 hours) in a solution consisting of 50% formamide and 0.2×SSC (1×SSC=0.15 M NaCl and 0.015 M of sodium citrate) at 20°-25° C. and then rinsed with a solution of 1×SSC. The filters were dried at 20° to 25° C. and exposed at −70° C. with and X-ray film (Kodak XR). FIG. 3 shows a typical result of such a test: on the surface represented, 1536 bacterial colonies were bred and screened by colony hybridization. The arrow indicates an example of a transformed bacteria clone the hybride plasmic DNA of which produces a signal with the radioactive sample. In all, by screening about 13,000 transformed bacterial colonies, 190 clones which produced a positive signal with the cDNA initiated by the tridecanucleotide and obtained from Namalwa cells induced with Sendai virus were isolated; they were collected on two microtitre plates (P1 and P2). Accordingly, about 1% of all the clones in the clone bank contained the specific sequence dCCTTCTGGAACTG.

EXAMPLE F

Figure 4:
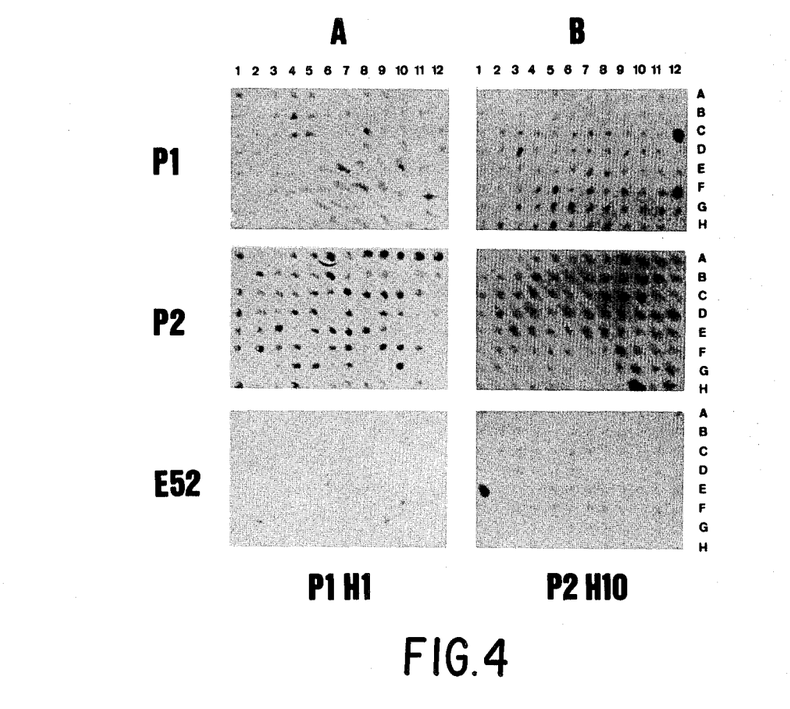
FIG. 4 is an illustration of the colony hybridization reaction of two polynucleotide-positive clones.

Analysis of the sequence complexity of the clones hybridizing with tridecanucleotide-primed cDNA In order to determine the number of clones with a different sequence (sequence complexity) in the 190 tridecanucleotide-positive clones (see Example E), the cDNA inserts were isolated from various clones by Pst I digestion (see Example C), electrophoresis in 0.8% agarose gels and elution of the desired bands (by precipitation of the fragment of gel containing the bands and electrophoretic elution of the DNA from the agarose in a dialysis tube) and these cDNA inserts were then labeled by nick translation with $^{32}$P using the method known from the literature (J. Mol. Biol. 113, 237–251 (1977)). Impressions of the tridecanucleotide-positive clones (microtitre plates P1 and P2) and of a randomly selected microtitre plate (E52) were transferred onto nitrocellulose filters, cultivated, prepared for colony hybridization (see Example E) and hybridized with the various 32P-labeled cDNA inserts. The hybridization was carried out as described in Example E, except that 50 μg/ml of poly(U) and 10 μg/ml of poly(I): poly(C) were also added to the hybridization solution and after hybridization the filters were washed in 50% formamide and 1×SSC. FIG. 4 shows the results of such an experiment with the inserts of clones P1H1 and P2H10 as the sample. (P1H1 is the clone at position H1 on the microtitre plate P1, whilst P2H10 has the position H10 on the microtitre plate P2.) It was found that clone P1H1 hybridizes with more than 90% of all tridecanucleotide-positive clones on plates P1 and P2 and also with some clones on plate E52 (FIG. 4, part A). The identity of many of these clone sequences was later confirmed by restriction analysis. Clone P2H10 hybridized not only with itself but also with the clones in positions 1 C12, 1F12 and E52E1 (FIG. 4, part B). Clones P1A6 and P2B10 were also analyzed in this way and each hybridized only with itself (this result is not shown in FIG. 4). It can be inferred from these results that, in the collection of 190 tridecanucleotide-positive clones, presumably less than 10 qualitatively different sequences are present, P1H1, P2H10, P1A6 and P2B10 being four such different sequences.

EXAMPLE G

RNA transfer hybridization

Figure 5:
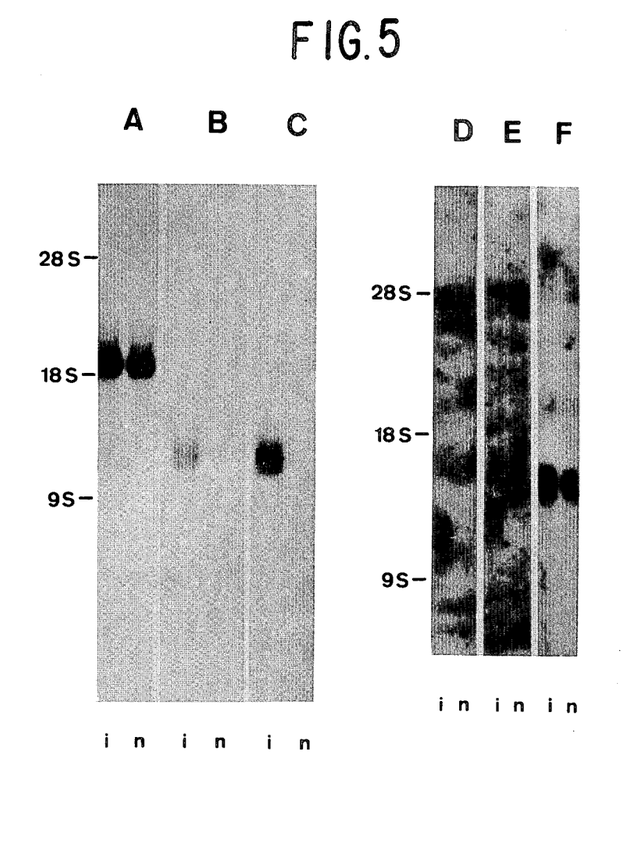
FIG. 5 is an autoradiograph of a hybridization of poly(A)+RNA with selected plasmids.

In order to find out whether a specific tridecanucleotide-positive bacterial clone could contain interferon sequences a test was made to see whether its plasmid DNA hybridizes with a mRNA induced in Namalwa cells by Sendai virus. For this purpose, poly(A)+RNA was isolated from induced and non-induced Namalwa cells analogously to the manner described in Example B, denatured by incubation for 1 hour at 50° C. in 1 M glyoxal, 50% DMSO, 10 mM of sodium phosphate buffer, pH 7, then separated on a 1.4% agarose gel, transferred onto nitrocellulose filter according to a method known from the literature (Proc. Nat. Acad. Sci. USA 77, 5201–5205 (1980)) and hybridized with plasmid DNA labeled with $^{32}$P by nick translation (see Example F). Plasmid DNA which is derived from an induced gene will only hybridize, in ths test arrangement, with RNA from induced cells, but not with RNA from non-induced cells. FIG. 5 shows the autoradiogrpahy of an experiment of this kind: induced RNA ("i") is in each ase in the left hand column of a pair, whilst non-induced RNA ("n") is in the right hand column. The plasmid DNAs used for hybridization are P1H1 (A), P1F12 (B,D), P2H10 (C), P1A6 (E), P2B10 (F). Of the plasmids tested, P1F12, P2H10 and P1A6 hybridized only with RNA from induced cells, whilst P1H1 and P2B10 also produced a signal with RNA from non-induced cells. The molecular size of the RNA hybridizing with P1F12 and P2H10 is 11-12S, whilst the size of the RNA hybridizing with P1A6 is 12-14S. These molecular sizes are known from the literature for IFN-$\beta$ and IFN-$\alpha$ mRNA. The plasmids P1F12, P2H10 and P1A6 were therefore invetigated further in order to determine clearly their content of interferon-DNA sequences.

EXAMPLE H

Biological detection of interferon activity in the translation products of hybrid-isolated RNA A demonstration based on biological testing to see whether a specific hybrid plasmid does or does not contain interferon-DNA sequences was carried out for the plasmids P1F12, P2H10, P1H1 and P2B10. The principle of this demonstration is as follows: the plasmid DNA to be tested is fixed on a nitrocellulose filter and then incubated, under conditions of hybridization, with poly(A)+RNA from induced Namalwa cells (see Example B). If the bonded DNA contains interferon sequences, interferon-mRNA will hybridize therewith. The non-hybridized RNA is subsequently washed away, the hybridized RNA is melted away from the DNA and injected into *Xenopus laevis* oocytes. Oocytes are capable of translating injected mRNA into proteins (see Example B). If the hybridized RNA is interferon-mRNA, interfern protein the antiviral properties of which can be demonstrated in the plaque reduction test (see Example A0 will be formed in the oocytes. In detail, this test is carried out as follows: 10 $\mu$g of linearized plasmid DNA was denatured in 200 $\mu$l of 0.5 N NaOH, neutralized with 200 $\mu$l of 0.5 N acetic acid+20×SET (for the composition of SET see Example E) and fixed by filtration on nitrocellulose filters ($\phi$2.5 cm). The filters were dried at ambient temperature, baked at 80° C. for 2 hours and then prehybridized for 1 hour at 53° C. or at 37° C. in 50% formamide, 20 mM PIPES, pH 6.5, 0.4 M NaCl, 5 mM EDTA, 10% dextrane sulphate, 1% SDS, 20 $\mu$g/ml of *Escherichia coli* tRNA and 50 $\mu$g/ml of poly(A) and then hybridized for 5 hours in the same buffer after the addition of 14-40 $\mu$g of induced Namalwa poly(A)+RNA. Then the filters were washed three times for 20 minutes at 25° C. in 0.2-1×SET, 0.2% SDS, 1% dextrane sulphate, 5 $\mu$g/ml of tRNA then twice for 10 minutes at 25° C. in 2 mM of EDTA, pH 8.0, 0.2% SDS, 1% dextrane sulphate and 5 $\mu$g/ml of tRNA, then once for 5 minutes at 60° C. in 2 mM of EDTA, pH 8.0, 0.2% SDS and 5 $\mu$g/ml of tRNA. The hybridized RNA was eluted for 4 minutes at 100° C. in 1 ml of H$_2$O+10 $\mu$g of tRNA. After chromatography on column of oligo(dT)cellulose (see Example B) the RNA was precipitated with ethanol, taken up in 5 $\mu$lf H$_2$O and injected into *Xenopus laevis* oocytes. After 2 days incubation at ambient temperature the oocyte supernatants were removed and tested, by the plaque reduction test, for interferon activity.

The results confirmed the assumption which was obvious from the RNA transfer hybridizations (Example G), namely that clones P1F12 and P2H10 carried interferon-DNA inserts, but that clones P1H1 and P2B10 did not. By neutralizing the resulting interferon activity with specific antisera against IFN-$\alpha$ or IFN-$\beta$ (see Example A) is was possible to show that the inserts in clones P1F12 and P2H10 are IFN-$\beta$ DNA sequences.

| Clone | Interferon activity (units/ml of oocyte supernatant) | Percentage neutralization by antiserum against | |
|---|---|---|---|
| | | IFN-$\alpha$ | IFN-$\beta$ |
| P1F12 | ~50 | — | 98 |
| P2H10 | ~50 | — | 98 |
| P1H1 | <2 | — | — |
| P2B10 | <2 | — | — |

EXAMPLE I

Restriction and sequence analysis of clones of the IFN-$\beta$ type

The cDNA inserts in clones P1F12 and P2H10 were investigated by means of restriction endonucleases, to determine the existence and possible positions of the breaks in the enzymes Bam HI, Bgl II, Eco RI, Hin dIII, Pst I and Pvu II. A comparison of the restriction maps of P1F12 and P2H10 with the gene for IFN-$\alpha$ known from the literature (Gene 10, 11-15 (1980)) is shown in FIG. 6: all three clones are cut by Pvu II, Pst I and Bgl II, the distances between the individual breaks being the same for each clone. As a final proof that the inserts in clones P1F12 and P2H10 were identical with the IFN-$\beta$ gene, parts of the DNA sequences ("on the right" (3') of the Pvu II and Bgl II cuts) were identified using the method of Maxam and Gilbert (Proc. Nat. Acad. Sci. USA 74, 560-564 (1977)) and compared with the published IFN-$\beta$ sequence. The sequences of P1F12 and P2H10 were shown to correspond exactly to the IFN-$\beta$ gene.

Neither clone has the complete IFN-$\beta$ sequence at the 5' end; they each lack about 60 nucleotides of the region which encodes for mature protein. At the 3' end, P1F12 is complete and P2H10 also contains the entire 3' region of IFN-$\beta$ cDNA, including the poly(dA) sequences derived from poly(A)RNA. However, P2H10 extends considerably further (1400 base pairs): 3' from the poly(dA) there is a region with the sequence oligo(dC), followed by a sequence of unknown origin; DNA sequence analysis of various fragments of this additional region of P2H10 showed no homology with the IFN-$\beta$ gene. It was further found that the clones P1C12 and E52E1 (described in Example F) cross-hybridizing with clone P2H10 hybridize with precisely this additional region of P2H10 and not with the IFN-$\beta$ part.

EXAMPLE J

Analysis of the IFN-$\alpha$-type clone P1A6

The clone p1a6 hybridizes with virus-induced Namalwa RNA in the region of 12-14S (described in Example G). It contains a cDNA insert of about 900 base pairs which, as shown by restriction analysis, does not have any breaks for the enzymes Bam HI, Bgl II, Eco RI, Hin dIII, Pst I and Pvu II (see FIG. 6).

The proof that the clone P1A6 contains IFN-α sequences was again provided by DNA sequence analysis; the sequence of the cDNA insert of P1A6 was determined inwardly from the Pst I breaks adjacent to the insert (see FIG. 8) and compared with the IFN-α sequences described by Goeddel et al (Nature 290, 20–26 (1981)). It was found that clone P1A6 is a variant of LeIFN C but 49 base pairs shorter. The presence of poly(A) sequences at the 3′ end of P1A6 indicates that clone P1A6 is derived from a shorter mRNA than the published clone LeIFN C. The region which encodes for LeIFN C protein is present in its entirety.

EXAMPLE K

Identification and analysis of another IFN-α-type clone (1F7)

Clone P1A6 was the only IFN-α-type clone which could be identified from the collection of 190 tridecanucletodie-positive clones (see Example E). In order to find further IFN-α-type clones, 1800 clones from the original cDNA clone bank (Example C) were hybridized with the cDNA insert of clone P1A6 by colony hybridization (as described in Example F). Another IFN-α clone (clone 1F7) was found in this way. Restriction analysis and partial DNA sequencing of the cDNA insert of 1F7 showed that 1F7 is a variant of the clone type LeIFN A (Goeddel et al, loc. cit.) but 175 base pairs longer. 1F7, like LeIFN A, contains two breaks for each of the enzymes Bgl II and Pvu II (FIG. 6).

The known DNA sequence of mature Le IFN-A (see D. V. Goeddel et al. in 287 Nature 413 (1980) and 290 Nature 20 (1981)) is as follows:

in the position from 120 to 327 of the DNA sequence the following differences:

In position 137 and 170 the nucleotide A was exchanged by the nucleotide G.

The remaining positions of the DNA sequence of clone 1F7 were also routinely determined by the standard methodology mentioned (Messing et al. and Gardner et al., supra). This demonstrated that 1F7 is a clone coding for the entire sequence of a mature interferon of the alpha-type, containing in addition a leader sequence and nontranslated flanking sequence at the 3′ and 5′ end, respectively. The non-coding region at the 3′ end is 162 bp longer than the corresponding sequence for IFN-αA from Goeddel, supra.

Therefore, from the sequence of the known mature IFN-αA, the sequence derived from clone 1F7, and the universal genetic code, the protein structure of the mature interferon obtained from clone 1F7 is as follows:

--- cys—asp—leu—pro—gln—thr—his—ser—leu—gly—ser—
—arg—arg—thr—leu—met—leu—leu—ala—gln—met—arg—
↓
—arg—ile—ser—leu—phe—ser—cys—leu—lys—asp—arg—
↓
—arg—asp—phe—gly—phe—pro—gln—glu—glu—phe—gly—
—asn—gln—phe—gln—lys—ala—glu—thr—ile—pro—val—
—leu—his—glu—met—ile—gln—gln—ile—phe—asn—leu—
—phe—ser—thr—lys—asp—ser—ser—ala—ala—trp—asp—
—glu—thr—leu—leu—asp—lys—phe—tyr—thr—glu—leu—
—tyr—gln—gln—leu—asn—asp—leu—glu—ala—cys—val—
—ile—gln—gly—val—gly—val—thr—glu—thr—pro—leu—
—met—lys—glu—asp—ser—ile—leu—ala—val—arg—lys—
—tyr—phe—gln—arg—ile—thr—leu—tyr—leu—lys—glu—
—lys—lys—tyr—ser—pro—cys—ala—trp—glu—val—val—
—arg—ala—glu—ile—met—arg—ser—phe—ser—leu—ser—
—thr—asn—leu—gln—glu—ser—leu—arg—ser—lys—glu.

---

| TGT | GAT | CTG | CCT | CAA | ACC | CAC | AGC | CTG | GGT | AGC |
|-----|-----|-----|-----|-----|-----|-----|-----|-----|-----|-----|
| AGG | AGG | ACC | TTG | ATG | CTC | CTG | GCA | CAG | ATG | AGG |
| AAA | ATC | TCT | CTT | TTC | TCC | TGC | TTG | AAG | GAC | AGA |
| CAT | GAC | TTT | GGA | TTT | CCC | CAG | GAG | GAG | TTT | GGC |
| AAC | CAG | TTC | CAA | AAG | GCT | GAA | ACC | ATC | CCT | GTC |
| CTC | CAT | GAG | ATG | ATC | CAG | CAG | ATC | TTC | AAT | CTC |
| TTC | AGC | ACA | AAG | GAC | TCA | TCT | GCT | GCT | TGG | GAT |
| GAG | ACC | CTC | CTA | GAC | AAA | TTC | TAC | ACT | GAA | CTC |
| TAC | CAG | CAG | CTG | AAT | GAC | CTG | GAA | GCC | TGT | GTG |
| ATA | CAG | GGG | GTG | GGG | GTG | ACA | GAG | ACT | CCC | CTG |
| ATG | AAG | GAG | GAC | TCC | ATT | CTG | GAC | GCT | GTG | AGG |
| AAA | TAC | TTC | CAA | AGA | ATC | ACT | CTC | TAT | CTG | AAA |
| GAG | AAG | AAA | TAC | AGC | CCT | TGT | GCC | TGG | GAG | GTT |
| GTC | AGA | GCA | GAA | ATC | ATG | AGA | TCT | TTT | TCT | TTG |
| TCA | ACA | AAC | TTG | CAA | GAA | AGT | TTA | AGA | AGT | AAG |
| GAA |     |     |     |     |     |     |     |     |     |     |

Originally, parts of the DNA sequence of the IFN-α-type clone (1F7) were analyzed according to the Dideoxy-method (see Messing et al in Nuc. Acid. Res. 9, 309 (1981) and Gardner, R. C. et al in Nuc. Acid. Res. 9, 2871 (1981)) with a Universal-primer. The following partial sequence for the positions 120 to 327 was found:

The arrows indicate the two differences between the IFN-αA (Goeddel, supra) and the mature IFN-α obtained from 1F7. At position 23, Le IFN-αA has a lysine whereas the IFN-from clone 1F7 has an arginine. At position 34, Le IFN-αA has a histidine, whereas the IFN-α from clone 1F7 has an arginine. The IFN-

```
      120
       |
..... CCTGGCACAGATGAGGAGAATCTCTCTTTTCTCCTGCTTGAAGGACAGAC
GTGACTTTGGATTTCCCCAGGAGGAGTTTGGCAACCAGTTCCAAAAGGCTGAAAC
CATCCCTGTCCTCCATGAGATGATCCAGCAGATCTTCAATCTCTTCAGCACAAAG
GACTCATCTGCTGCTTGGGATGAGACCCTCCTAGACAAATTCTA......
                                                  |
                                                 327
```

In comparison to the known sequence of IFN-αA type (see D. V. Goeddel et al in Nature 290, 20 (1981)) the new DNA-sequence of IFN-α-type clone (1F7) shows derived from clone 1F7 is therefore named "IFN-α-2 arg."

EXAMPLE L

Interferon activity in lysates of *E. coli* HB101, transformed with the hybrid plasmid 1F7

Lysates of bacterial cultures transformed with P1A6 or 1F7 were investigated for their content of biologically active interferon. For this, 100 ml of bacterial culture were cultivated in an L broth medium to give an optical density of 0.6–0.8, pelleted by centrifuging for 10 minutes at 7000 rpm, washed once in 50 mM of tris HCl, pH 8, and 30 mM of NaCl and finally suspended in 1.5 ml of the same buffer. After incubation with 1 mg/ml of lysozyme for 30 minutes over ice, the bacteria were frozen and thawed five times and then the cell fragments were removed by centrifuging for 1 hour at 40,000 rpm. The supernatant was sterilized by filtration and tested for interferon activity in the plaque reduction test. About 500 units per ml of interferon could be detected in lysates of clone 1F7 obtained in this way; in this test clone 1A6 did not produce any activity, which is presumably due to a different orientation of the insert in the plasmid vector.

EXAMPLE M

Improvement in the expression of the type of interferon encoded by 1F7

To achieve good expression of a gene, three conditions must be satisfied in terms of the DNA: first, there must be a promoter (an RNA-polymerase binding point) in front of the gene, secondly the RNA read off in front of the initiation codon of the translation must carry a ribosome binding sequence (RBS) and thirdly the distance between the RBS and the initiation codon must be of a suitable length.

For expressing the interferon coded by 1F7, the promoter sequence used was the promoter of the tryptophan operon of *Serratia marcescens* known from the literature (Nature 276, 684–689 (1978)) and the RBS used was a DNA sequence known from the literature (Proc. Natl. Acad. Sci. USA 78, 5543–5548 (1981)). In order to determine the optimum distance between the RBS and the initiation codon of 1F7 the following strategy was used: the 1F7-cDNA sequence was briefly digested with the exonuclease BAl 31 specific to double-stranded DNA, so as to produce a mixture of molecules of different lengths. These molecules were then ligated in a suitable manner using synthetic linker sequences to form an "expression plasmid," namely a plasmid which contained both promoter and RBS. *Escherichia coli* HB101 was transformed with these plasmids and individual transformants were tested for interferon production.

In detail, the test was carried out as follows: 0.5–1 μg of 1F7 insert was incubated in 100 μl of 20 mM tris HCl, pH 8.1, 0.6 M NaCl, 12 mM of MgCl$_2$, 12 mM of CaCl$_2$ and 1 mM of EDTA for 3 minutes at 30° C. with 0.5 units of BAL 31 (Bethesda Research Laboaratories). Then the reaction was stopped by the addition of 300 μl of 15 mM of EDTA, pH 7.8, the reaction mixture was heated to 65° C. for 10 minutes, extracted with phenol and ether and precipitated with ethanol. The precipitate was taken up in 10 μl of 70 mM tris HCl, pH 7.5, 7 mm of MgCl$_2$, 1 mM of DTT, 0.4 mM of ATP together with 30–60 pMol of phosphorylated Hin dIII linkers (Bethesda Research Laboratories) and incubated overnight at 14° C. with 0.5–1 unit of T4 ligase (Bethesda Research Laboratories). The reaction was stopped by heating to 65° C. for 10 minutes, then 2 M of NH$_4$ acetate were added and the interferon genes were freed from non-ligated linkers by precipitation with 0.6 volumes of isopropanol. The precipitation was dissolved in 30–50 μl of 33 mM tris acetate, pH 7.9, 66 mM K acetate, 10 mM Mg acetate and 100 μg/ml of BSA and digested for 2 to 3 hours with 30–50 units of Hin dIII. The reaction was stopped by heating to 65° C. for 10 minutes and, after the addition of 2 M NH$_4$ acetate, the interferon genes were precipitated with 0.6 volumes of isopropanol. The precipitete was dissolved in 10 μl of 70 mM tris HCl, pH 7.5, 7 mM MgCl$_2$, 1 mM of DTT and 0.5 mM of ATP and ligated overnight at 14° C. using $10^{-2}$ units of T4 ligase with 0.2 μg of Hin dIII-linearized, phosphatase-treated expression plasmid pER103. pER103 is a pBR322 derivative which contains the promoter sequence of the tryptophan operon of *S. marcescens* and an RBS known from the literature (see above); it can be linearized with Hin dIII in the vicinity of the RBS. The plasmids thus obtained are used for the transformation of *Escherichia coli* HB101 and the interferon production of individual transformants was tested in the manner described in Example L. There was found to be an increase in interferon expression up to about $10^4$ times that of spontaneous expression.

The properties mentioned above demonstrate that the recombinant DNA-molecules prepared according to the invention contain sequences which code for α- or β-interferon, the expression of interferon of type α being shown by means of one of these plasmids obtained according to the invention.

For example, the following microorganisms and recombinant DNA molecules were deposited at the "Deutsche Sammlung von Mikro-Organismen, Grisebachstrasse 8, 3400 Gottingen," on May 17, 1982 under the DSM numbers 2362 (1F7), 2363 (P1A6)
2364 (P1F12) and
2365 (P2H10)

and are accessible to the public according to the convention of Budapest.

What is claimed as new and desired to be secured by Letters Patent of the United States is:

1. A recombinant DNA (rDNA) molecule comprising a genetic sequence coding for a derivative of human alpha interferon, wherein said derivative comprises the following polypeptide formula:

cys—asp—leu—pro—gln—thr—his—ser—leu—gly—ser—
arg—arg—thr—leu—met—leu—leu—ala—gln—met—arg—
arg—ile—ser—leu—phe—ser—cys—leu—lys—asp—arg—
arg—asp—phe—gly—phe—pro—gln—glu—glu—phe—gly—
asn—gln—phe—gln—lys—ala—glu—thr—ile—pro—val—
leu—his—glu—met—ile—gln—gln—ile—phe—asn—leu—
phe—ser—thr—lys—asp—ser—ser—ala—ala—trp—asp—
glu—thr—leu—leu—asp—lys—phe—tyr—thr—glu—leu—
tyr—gln—gln—leu—asn—asp—leu—glu—ala—cys—val—
ile—gln—gly—val—gly—val—thr—glu—thr—pro—leu—
met—lys—glu—asp—ser—ile—leu—ala—val—arg—lys—
tyr—phe—gln—arg—ile—thr—leu—tyr—leu—lys—glu—
lys—lys—tyr—ser—pro—cys—ala—trp—glu—val—val—
arg—ala—glu—ile—met—arg—ser—phe—ser—leu—ser—
thr—asn—leu—gln—glu—ser—leu—arg—ser—lys—glu.

2. The rDNA molecule of claim 1 which is a plasmid capable of expression in *E. coli*.

3. A microorganism transformed with a recombinant DNA molecule comprising a genetic sequence coding for a derivative of human alpha-interferon, wherein said derivative comprises the following polypeptide formula:

cys—asp—leu—pro—gln—thr—his—ser—leu—gly—ser—
arg—arg—thr—leu—met—leu—leu—ala—gln—met—arg—
arg—ile—ser—leu—phe—ser—cys—leu—lys—asp—arg—
arg—asp—phe—gly—phe—pro—gln—glu—glu—phe—gly—
asn—gln—phe—gln—lys—ala—glu—thr—ile—pro—val—
leu—his—glu—met—ile—gln—gln—ile—phe—asn—leu—
phe—ser—thr—lys—asp—ser—ser—ala—ala—trp—asp—
glu—thr—leu—leu—asp—lys—phe—tyr—thr—glu—leu—
tyr—gln—gln—leu—asn—asp—leu—glu—ala—cys—val—
ile—gln—gly—val—gly—val—thr—glu—thr—pro—leu—
met—lys—glu—asp—ser—ile—leu—ala—val—arg—lys—
tyr—phe—gln—arg—ile—thr—leu—tyr—leu—lys—glu—
lys—lys—tyr—ser—pro—cys—ala—trp—glu—val—val—
arg—ala—glu—ile—met—arg—ser—phe—ser—leu—ser—
thr—asn—leu—gln—glu—ser—leu—arg—ser—lys—glu.

4. The micoorganisms of claim 3 wherein said microorganism is *E. coli.*

5. A method of producing an interferon alpha derivative which comprises:

transforming an organism with a recombinant DNA molecule comprising a genetic sequence coding for a derivative of human alpha-interferon, wherein said derivative comprises the following polypeptide formula:

cys—asp—leu—pro—gln—thr—his—ser—leu—gly—ser—
arg—arg—thr—leu—met—leu—leu—ala—gln—met—arg—
arg—ile—ser—leu—phe—ser—cys—leu—lys—asp—arg—
arg—asp—phe—gly—phe—pro—gln—glu—glu—phe—gly—
asn—gln—phe—gln—lys—ala—glu—thr—ile—pro—val—
leu—his—glu—met—ile—gln—gln—ile—phe—asn—leu—
phe—ser—thr—lys—asp—ser—ser—ala—ala—trp—asp—
glu—thr—leu—leu—asp—lys—phe—tyr—thr—glu—leu—
tyr—gln—gln—leu—asn—asp—leu—glu—ala—cys—val—
ile—gln—gly—val—gly—val—thr—glu—thr—pro—leu—
met—lys—glu—asp—ser—ile—leu—ala—val—arg—lys—
tyr—phe—gln—arg—ile—thr—leu—tyr—leu—lys—glu—
lys—lys—tyr—ser—pro—cys—ala—trp—glu—val—val—
arg—ala—glu—ile—met—arg—ser—phe—ser—leu—ser—
thr—asn—leu—gln—glu—ser—leu—arg—ser—lys—glu.

expressing said sequence coding for said derivative; and recovering said IFN-alpha derivative.

6. The method of claim 5 wherein said microorganism is *E. coli.*

7. An IFN-alpha derivative substantially free of other, different, IFN-alpha derivatives, produced by transforming an organism with a recombinant DNA molecule comprising a genetic sequence coding for a derivative of human alpha-interferon, wherein said derivative comprises the following polypeptide formula:

cys—asp—leu—pro—gln—thr—his—ser—leu—gly—ser—
—arg—arg—thr—leu—met—leu—leu—ala—gln—met—arg—
—arg—ile—ser—leu—phe—ser—cys—leu—lys—asp—arg—
—arg—asp—phe—gly—phe—pro—gln—glu—glu—phe—gly—
—asn—gln—phe—gln—lys—ala—glu—thr—ile—pro—val—
—leu—his—glu—met—ile—gln—gln—ile—phe—asn—leu—
—phe—ser—thr—lys—asp—ser—ser—ala—ala—trp—asp—
—glu—thr—leu—leu—asp—lys—phe—tyr—thr—glu—leu—
—tyr—gln—gln—leu—asn—asp—leu—glu—ala—cys—val—
—ile—gln—gly—val—gly—val—thr—glu—thr—pro—leu—
—met—lys—glu—asp—ser—ile—leu—ala—val—arg—lys—
—tyr—phe—gln—arg—ile—thr—leu—tyr—leu—lys—glu—
—lys—lys—tyr—ser—pro—cys—ala—trp—glu—val—val—
—arg—ala—glu—ile—met—arg—ser—phe—ser—leu—ser—
—thr—asn—leu—gln—glu—ser—leu—arg—ser—lys—glu expressing said sequence coding for said derivative; and recovering said IFN-alpha derivative.

8. An interferon alpha derivative comprising the following formula:

cys—asp—leu—pro—gln—thr—his—ser—leu—gly—ser—
—arg—arg—thr—leu—met—leu—leu—ala—gln—met—arg—
—arg—ile—ser—leu—phe—ser—cys—leu—lys—asp—arg—
—arg—asp—phe—gly—phe—pro—gln—glu—glu—phe—gly—
—asn—gln—phe—gln—lys—ala—glu—thr—ile—pro—val—
—leu—his—glu—met—ile—gln—gln—ile—phe—asn—leu—
—phe—ser—thr—lys—asp—ser—ser—ala—ala—trp—asp—
—glu—thr—leu—leu—asp—lys—phe—tyr—thr—glu—leu—
—tyr—gln—gln—leu—asn—asp—leu—glu—ala—cys—val—
—ile—gln—gly—val—gly—val—thr—glu—thr—pro—leu—
—met—lys—glu—asp—ser—ile—leu—ala—val—arg—lys—
—tyr—phe—gln—arg—ile—thr—leu—tyr—leu—lys—glu—
—lys—lys—tyr—ser—pro—cys—ala—trp—glu—val—val—
—arg—ala—glu—ile—met—arg—ser—phe—ser—leu—ser—
—thr—asn—leu—gln—glu—ser—leu—arg—ser—lys—glu substantially free of other, different, interferon alpha derivatives.

* * * * *